(12) United States Patent
Chheda et al.

(10) Patent No.: US 10,005,749 B2
(45) Date of Patent: Jun. 26, 2018

(54) CLOSED-LOOP PRODUCTION OF FURFURAL FROM BIOMASS

(71) Applicant: SHELL OIL COMPANY, Houston, TX (US)

(72) Inventors: Juben Nemchand Chheda, Houston, TX (US); Jean Paul Andre Marie Joseph Ghislain Lange, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 0 days. days.

(21) Appl. No.: 15/502,808

(22) PCT Filed: Aug. 13, 2015

(86) PCT No.: PCT/US2015/044994
§ 371 (c)(1),
(2) Date: Feb. 9, 2017

(87) PCT Pub. No.: WO2016/025679
PCT Pub. Date: Feb. 18, 2016

(65) Prior Publication Data
US 2017/0233360 A1    Aug. 17, 2017

Related U.S. Application Data

(60) Provisional application No. 62/037,171, filed on Aug. 14, 2014.

(51) Int. Cl.
C07D 307/50    (2006.01)
(52) U.S. Cl.
CPC ................ *C07D 307/50* (2013.01)

(58) Field of Classification Search
CPC .................................................. C07D 307/50
(Continued)

(56) References Cited

U.S. PATENT DOCUMENTS

| | | |
|---|---|---|
| 2,078,241 A | 4/1937 | Fulmer et al. |
| 4,409,032 A | 10/1983 | Paszner et al. |

(Continued)

FOREIGN PATENT DOCUMENTS

| | | |
|---|---|---|
| WO | 2007009463 | 1/2007 |
| WO | 2012041990 | 4/2012 |

(Continued)

OTHER PUBLICATIONS

Galbe et al.; "A review of the productiom of ethanol from softwood"; Appl Microbiol Biotechnol; vol. 59; pp. 618-628; 2002.

(Continued)

*Primary Examiner* — Taylor V Oh

(57) ABSTRACT

Methods and processes for the production of valuable organic products and alcohols from biomass material using a closed-loop process having numerous advantages over prior production methods are described. In the process, the biomass is subjected to acid-catalyzed digestion, followed by a separation of the digestion product stream into a solid product stream and a liquid product stream, the liquid product stream thereafter undergoing acid-catalyzed dehydration in the presence of an organic solvent, and thereafter separating the organic products in the organic layer from the aqueous layer. During the process, aqueous and organic fluid streams are fed back into various portions of the production process to increase the concentration of active portions and maximize product recovery.

13 Claims, 8 Drawing Sheets

(58) Field of Classification Search
USPC .......................................................... 549/489
See application file for complete search history.

(56) References Cited

U.S. PATENT DOCUMENTS

| | | | |
|---|---|---|---|
| 4,461,648 | A | 7/1984 | Foody |
| 5,820,687 | A | 10/1998 | Farone et al. |
| 8,168,807 | B2 | 5/2012 | Wabnitz et al. |
| 8,466,242 | B2 | 6/2013 | Geremia et al. |
| 2010/0001919 | A1 | 1/2010 | Hoffer et al. |
| 2012/0107887 | A1 | 5/2012 | Chheda et al. |
| 2012/0122152 | A1 | 5/2012 | Blackbourn et al. |
| 2012/0157697 | A1 | 6/2012 | Burket et al. |
| 2012/0302765 | A1 | 11/2012 | Dumesic et al. |
| 2013/0295629 | A1 | 11/2013 | Weider et al. |
| 2014/0018555 | A1 | 1/2014 | DeVries et al. |

FOREIGN PATENT DOCUMENTS

| | | |
|---|---|---|
| WO | 2016025678 | 2/2016 |
| WO | 2016025679 | 2/2016 |

OTHER PUBLICATIONS

Ong; "Conversion of Lignocellulosic Biomass to Fuel Ethanol—A Brief Review"; The Planter; vol. 80, No. 941; pp. 517-524; 2004.
Moller; "Cell Wall Saccharification"; Outputs from the EPOBIO project; 69 pages; Nov. 2006.
Holtzapple et al.; "The Ammonia Freeze Explosion (AFEX) Process; A Practical Lignocellulose Pretreatment"; Applied Biochemistry and Biotechnology; vol. 28/29; pp. 59-74; 1991.
Kumar et al; "Methods for Pretreatment of Lignocellulosic Biomass for Efficient Hydrolysis and Biofuel Production"; Ind. Eng. Chem Res; vol. 48; pp. 3713-3729; 2009.
Lavarack et al.; The acid hydrolysis of sugarcane bagasse hemicellulose to produce xylose, arabinose, glucose and other products; Biomass and Bioenergy; vol. 23; pp. 367-380; 2002.
Yang et al.; "One-Step Catalytic Transformation of Carbohydrates and Cellulosic Biomass to 2,5-Dimethyltetrahydrofuran for Liquid Fuels"; Chem. Sus. Chem.; vol. 3; pp. 597-603; 2010.
International Search Report for PCT/2015/044994 dated Sep. 28, 2015; 4 pages.
Lange et al.; "Furfural—A Promising Platform for Lignocellulosic Biofuels"; Chem Sus Chem; vol. 5, pp. 150-166; 2012.

CLOSED-LOOP PRODUCTION OF FURFURAL FROM BIOMASS

PRIORITY CLAIM

The present application is the National Stage (§ 371) of International Application No. PCT/US2015/044994, filed Aug.13, 2015, which claims priority from U.S. Provisional Application No. 62/037,171, filed Aug. 14, 2014 incorporated herein by reference.

BACKGROUND OF THE INVENTION

Field of the Invention

The inventions disclosed and taught herein relate generally to processes for treating biomass, and more specifically to the treatment of biomass feedstocks for the production of furfural and similar organic compounds and/or intermediates using a closed loop production process.

Description of the Related Art.

Lignocellulosic biomass is viewed as an abundant renewable resource for fuels and chemicals due to the presence of sugars in the cell walls of plants. More than 50% of the organic carbon on the earth's surface is contained in plants. This lignocellulosic biomass is comprised of hemicelluloses, cellulose and smaller portions of lignin and protein. Cellulose is a polymer comprised mostly of condensation polymerized glucose and hemicellulose is a precursor to pentose sugars, mostly xylose. These sugars can easily be converted into fuels and valuable components, provided they can be liberated from the cell walls and polymers that contain them. However, plant cell walls have evolved considerable resistance to microbial, mechanical or chemical breakdown to yield component sugars. A number of approaches to overcome this recalcitrance have been performed and the breakdown of these polymers into sugars, saccharification, has a long history. General methods are outlined schematically in FIG. 1.

The original approaches dating back to the early 19th century involve complete chemical hydrolysis using concentrated mineral acids such as hydrochloric acid, nitric, or sulfuric acid. Numerous improvements to these processes have been made earning higher sugar yields from the biomass feedstock. These higher acid concentration approaches provide higher yields of sugars, but due to economic and environmental reasons, the acids must be recovered. The primary obstacle to practicing this form of saccharification has been the challenges associated with recovery of the acid [M. Galbe and G. Zacchi, *Appl. Microbiol. Biotechnol.* Vol. 59, pp. 618-628 (2002)]. Recent efforts toward separating sulfuric acid and sugars using ion resin separation or hydrochloric acid and sugars via an amine extraction process and subsequent thermal regeneration of the acid have been described in U.S. Pat. No. 5,820,687. However, both of these approaches are cumbersome and expensive in practice.

Dilute acid processes have also been attempted to perform chemical saccharification and one such example is the Scholler-Tornesch Process. However, usage of dilute acid requires higher temperatures and this usually results in low yields of the desired sugars due to thermal degradation of the monsaccharides. Numerous approaches of this type have been made in the past and all have failed to meet economic hurdles. [See, for example, Lim Koon Ong, "Conversion of Lignocellulosic Biomass to Fuel Ethanol—A Brief Review," *The Planter*, Vol. 80, No. 941, August 2004, and, "Cell Wall Saccharification," Ralf Moller, in Outputs from the EPOBIO Project, 2006; Published by CPL Press, Tall Gables, The Sydings, Speen, Newbury, Berks RG14 1RZ, UK].

The saccharification of the cellulose enzymatically holds promise of greater yields of sugars under milder conditions and is therefore considered by many to be more economically attractive. The recalcitrance of the raw biomass to enzymatic hydrolysis necessitates a pretreatment to enhance the susceptibility of the cellulose to hydrolytic enzymes. A number of pretreatment methods, such as described by Mosier, et al. [*Bioresource Technology*, Vol. 96, pp. 673-686 (2005)], have been developed to alter the structural and chemical composition of biomass to improve enzymatic conversion. Such methods include treatment with a dilute acid steam explosion, as described in U.S. Pat. No. 4,461,648, hydrothermal pretreatment without the addition of chemicals as described in WO 2007/009463 A2, ammonia freeze explosion process as described by Holtzapple, M. T., et al. [*Applied Biochemistry and Biotechnology*, 28/29, pp. 59-74], and an organosolve extraction process described in U.S. Pat. No. 4,409,032. Despite these approaches, such pretreatment has been cited as the most expensive process in biomass-to-fuels conversion [*Ind. Eng. Chem. Res.*, Vol. 48(8), 3713-3729. (2009)].

One pretreatment that has been extensively explored is a high temperature, dilute-sulfuric acid ($H_2SO_4$) process, which effectively hydrolyzes the hemicellulosic portion of the biomass to soluble sugars and exposes the cellulose so that enzymatic Saccharification is successful. The parameters which can be employed to control the conditions of the pretreatment are time, temperature, and acid loading. These are often combined in a mathematical equation termed the combined severity factor. In general, the higher the acid loading employed, the lower the temperature that can be employed; this comes at a cost of acid and its need to recycle the acid. Conversely, the lower the temperature, the longer the pretreatment process takes; this comes at the cost of volumetric productivity. It is desirable to lower the temperature because pentose sugars readily decompose to form furfural and other species which represents a yield loss and these compounds are poisons to downstream fermentation. However, the use of the higher concentrations of acid required to lower the pretreatment temperatures below that where furfural formation becomes facile [B. P. Lavarack, et al., *Biomass and Bioenergy*, Vol. 23, pp. 367-380 (2002)] once again requires the recovery of the strong acid. If dilute acid streams and higher temperatures are employed the pretreatment reaction produces increased amounts of furfural and the acid passing downstream to the enzymatic hydrolysis and subsequent fermentation steps must be neutralized resulting in inorganic salts which complicates downstream processing and requires more expensive waste water treatment systems. This also results in increased chemical costs for acid and base consumption.

The inventions disclosed and taught herein are directed to methods for the synthesis of furfural and similar organic materials from a biomass feedstock using a closed-loop system that allows for the aqueous streams containing acid from hydrolysis steps to be largely recycled into the production system.

SUMMARY OF THE INVENTION

The objects described above and other advantages and features of the invention are incorporated in the application as set forth herein, and the associated appendices and drawings, related to systems and methods for the synthesis of furfural and other organic intermediate compounds from a biomass feedstock using a closed-loop aqueous stream system.

In accordance with a first embodiment of the present disclosure, a closed-loop process for converting biomass into furfural, the process comprising the steps of:
(a) providing a pentosan-containing biomass material;
(b) subjecting the pentosan-containing biomass material to an acid catalyzed digestion process in a digestion vessel at a temperature greater than about 100° C. for a period of time sufficient to produce a digested product stream comprising $C_5$-carbohydrates and solids comprising cellulose;
(c) separating the digested product stream into a liquid product stream and a solid product stream, the liquid product stream comprising carbohydrate compounds, of which carbohydrate compounds at least 50 wt % are $C_5$—carbohydrate compounds, based on the weight of carbohydrate compounds in the liquid product stream, and the solid product stream comprising solids comprising cellulose;
(d) subjecting the $C_5$-carbohydrate in the liquid product stream to a dehydration reaction in a reaction vessel at a temperature in the range of from about 100° C. to about 250° C. in the presence of an acid catalyst and a biphasic mixture comprising an aqueous phase and a water-immiscible organic phase, which comprises an organic solvent, for a period of time sufficient to produce furfural or a furan derivative;
(e) retrieving from the reaction vessel a dehydration product stream comprising water, organic solvent and comprising furfural and separating the dehydration product stream into an aqueous recycle stream and an organic product stream comprising furfural;
(f) recycling the aqueous recycle stream back into the digestion vessel in step (b); and
(g) extracting the furfural from the organic product stream by at least one separation process.

The above paragraphs present a simplified summary of the presently disclosed subject matter in order to provide a basic understanding of some aspects thereof. The summary is not an exhaustive overview, nor is intended to identify key or critical elements to delineate the scope of the subject matter described and claimed herein. Its sole purpose is to present some concepts in a simplified form as a prelude to the more detailed description set forth below.

BRIEF DESCRIPTION OF THE DRAWINGS

The following figures form part of the present specification and are included to further demonstrate certain aspects of the present invention. The invention may be better understood by reference to one or more of these figures in combination with the detailed description of specific embodiments presented herein.

Figure 1:
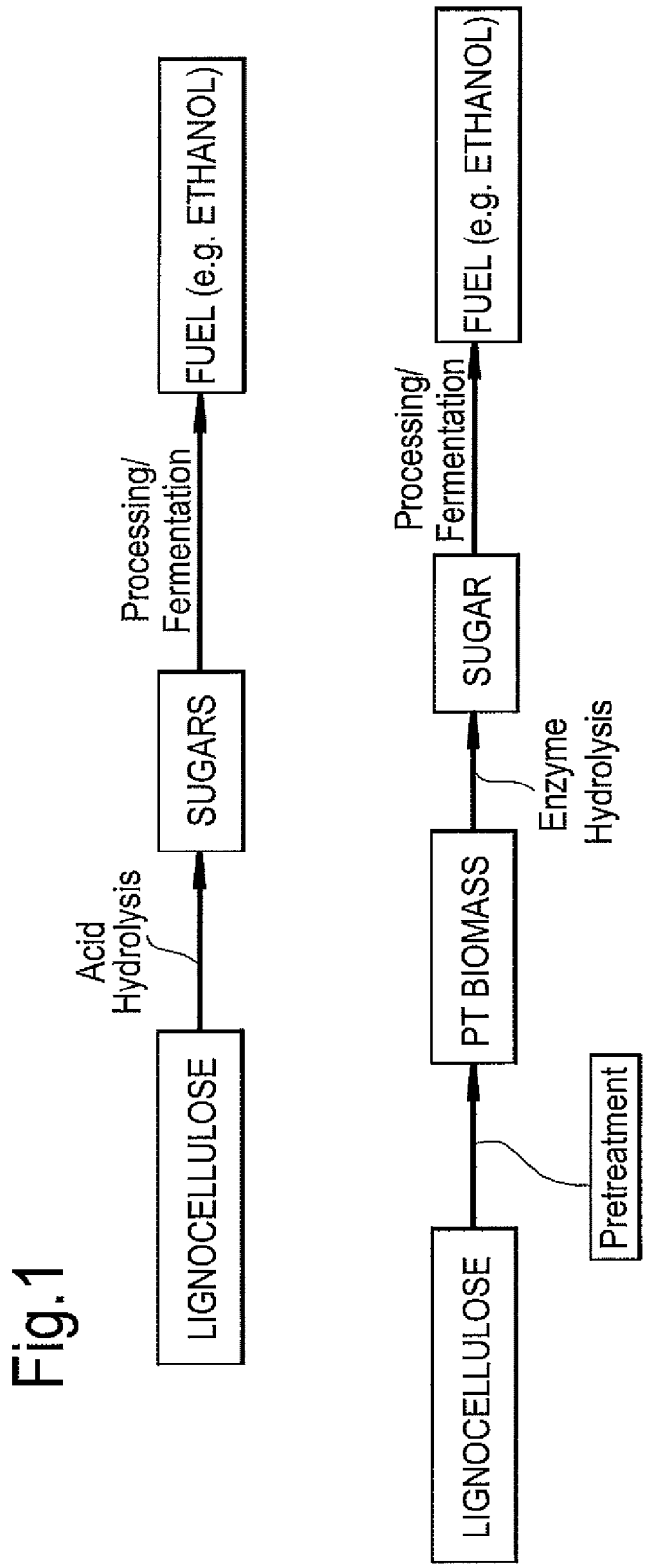
FIG. 1 illustrates a block flow diagram of lignocellulose treatment methods.

While the inventions disclosed herein are susceptible to various modifications and alternative forms, only a few specific embodiments have been shown by way of example in the drawings and are described in detail below. The figures and detailed descriptions of these specific embodiments are not intended to limit the breadth or scope of the inventive concepts or the appended claims in any manner. Rather, the figures and detailed written descriptions are provided to illustrate the inventive concepts to a person of ordinary skill in the art and to enable such person to make and use the inventive concepts.

Definitions

The following definitions are provided in order to aid those skilled in the art in understanding the detailed description of the present invention. Unless otherwise defined herein, scientific and technical terms used in connection with the present invention shall have the meanings that are commonly understood by those of ordinary skill in the art to which this invention belongs. Further, unless otherwise required by context, singular terms shall include pluralities and plural terms shall include the singular.

Unless explicitly stated otherwise in defined circumstances, all percentages, parts, ratios, and like amounts used herein are defined by weight.

Further, in this connection, certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination.

The articles "a" and "an" may be employed in connection with various elements and components of compositions, processes or structures described herein. This is merely for convenience and to give a general sense of the compositions, processes or structures. Such a description includes "one or at least one" of the elements or components. Moreover, as used herein, the singular articles also include a description of a plurality of elements or components, unless it is apparent from a specific context that the plural is excluded.

The term "about" means that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about", the claims include equivalents to the quantities. The term "about" may mean within 10% of the reported numerical value, preferably within 5% of the reported numerical value.

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, the ranges set forth herein include their endpoints unless expressly stated otherwise. Further, when an amount, concentration, or other value or parameter is given as a range, one or more preferred ranges or a list of upper preferable values and lower preferable values, this is to be understood as specifically disclosing all ranges formed from any pair of any upper range limit or preferred value and any lower range limit or preferred value, regardless of whether such pairs are separately disclosed. The scope of the invention is not limited to the specific values recited when defining a range.

The term "contacting", as used herein, refers to the process of bringing into contact at least two distinct species such that they can react. It will be appreciated, however, that the resulting reaction product can be produced directly from a reaction between the added reagents or from an intermediate from one or more of the added reagents which can be produced in the reaction mixture.

The term "biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar, protein and oil such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like. In some embodiments, the lignocellulosic biomass is selected from the group including, but not limited to, corn stover, straw, bagasse, miscanthus, sorghum residue, switch grass, bamboo, water hyacinth, hardwood, hardwood, softwood, wood chips, and wood pulp.

As used herein the term "pentosan" refers to a polysaccharide containing $C_5$ carbohydrates monomers.

As used herein, the term "carbohydrate" is defined as a compound that consists only of carbon, hydrogen, and oxygen atoms, wherein the ratio of carbon atoms to hydrogen atoms to oxygen atoms is 1:2:1. Well known examples of carbohydrates include sugars and sugar-derived oligomers and sugar-derived polymers.

The term "$C_5$ carbohydrates" refers to any carbohydrate, without limitation, that has five (5) carbon atoms in its monomeric unit. The definition includes pentose sugars of any description and stereoisomerism (e.g., D/L aldopentoses and D/L ketopentoses). $C_5$ carbohydrates can include (by way of example and not limitation) arabinose, lyxose, ribose, ribulose, xylose, and xylulose, in their monomeric, oligomeric and polymeric forms. Polymeric $C_5$ carbohydrates can contain several $C_5$ carbohydrate monomers and in some instances even contain some (lesser) amount of $C_6$ carbohydrate monomers.

The term "$C_6$ carbohydrate" refers to any carbohydrate, without limitation, that has six (6) carbon atoms in its monomeric unit. The definition includes hexose sugars of any description and stereoisomerism (e.g., D/L aldohexoses and D/L ketohexoses). $C_6$ carbohydrates include (by way of example and not limitation) allose, altrose, fructose, galactose, glucose, gulose, idose, mannose, psicose, sorbose, tagatose, and talose, in their monomeric, oligomeric and polymeric forms. Polymeric $C_6$ carbohydrates can contain several $C_6$ carbohydrate monomers, and in some instances even contain some (lesser) amount of $C_5$ carbohydrate monomers.

"Cellulose", as used herein, refers to a polysaccharide of glucose monomers ($(C_6H_{10}O_5)_n$); the term "cellulosic biomass" as used herein refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose and other $C_5$ carbohydrates, as does hemicellulose.

As used herein, the term "lignocellulosic" means, comprising cellulose, lignin and hemicellulose.

As used herein, the term "hemicellulosic" refers to a material comprising $C_5$ and $C_6$ sugar polymers. Hemicellulose consists of short, highly branched chains of sugars. It contains five-carbon sugars (usually D-xylose and L-arabinose) and six-carbon sugars (D-galactose, D-glucose, and D-mannose) and uronic acid, as well as some deoxy sugars in select instances. The sugars are partially acetylated. Typically, the acetyl content is 10 to 15 wt %, based on the hemicellulose or 2 to 3 wt %, based on the biomass.

As used herein, the term "lignin" or "lignin feed" in the process of this invention refers to a polyphenois material comprised of phenolyl propane units linked by carbon oxygen and carbon-carbon bonds. Lignins can be highly branched and can also be crosslinked. Lignins can have significant structural variation that depends, at least in part, on the plant source involved. Lignin is present as virgin lignin in unprocessed lignocellulosic materials. However, lignins also include any type of lignin material that is extracted or produced from lignocellulose, independent of its source of method of production. Suitable lignin materials include, but are not limited to, Kraft lignins (a by-product of the paper industry), organosolve lignins, lignins derived as a byproduct of ethanol production processes, lignins derived from waste, including municipal waste, lignins derived from wood or wood products, as well as from agricultural products or waste, and various combinations thereof.

The term "elevated pressure," in the context of the processes of the present invention, refers to a pressure above atmospheric pressure (e.g., 1 atm at sea level) based on the elevation, for example at least 20, 30, 40, 50, 60, 70, 80, 90, 100, 110, 120, 130, 140, 150, 160, 170, 180, 190, 200, 225, 250, 275, 300, 325, 350, 375, or 400 psi (or greater), as well as pressures between any two of these values (e.g., 185 psi or 215 psi) at sea level.

The term "elevated temperature," as used herein, refers to a temperature above ambient temperature, for example at least about 100, 110, 120, 130, 140, 150, 160, 170, 180, 190, 200, 210, 220, 230, 240, or 250 degrees Celsius (° C.) or greater.

The term "dehydration", as used herein, refers to the removal of a water molecule from a molecule that contains at least one hydroxyl group.

The term "hydrolysis" as used herein refers to breaking the glycosidic bonds in polysaccharides to yield simple monomeric and/or oligomeric sugars. For example, hydrolysis of cellulose produces the six carbon ($C_6$) sugar glucose, whereas hydrolysis of hemicellulose produces the five carbon ($C_5$) sugars xylose and arabinose together with other sugars. Hydrolysis can be accomplished by acid treatment or by enzymes such as cellulase, β-glucosidase, and xylanase.

The term "tar", as used herein, refers to the generic reference to organic material which is insoluble in water, which is dark in color, and which tends to become viscous and very dark to almost black when concentrated. Tar can be formed during heating of organic material, for example by pyrolysis, but is also formed when carbohydrates are subjected to acid hydrolysis, particularly when done at high temperatures. The presence of tar is undesired for a number of reasons. The tar may negatively affect the production of the bio-based product in the application. For this reason tar is preferably removed before further steps.

As used herein, the term "humins" refers to the dark, amorphous and undesirable acid byproducts and resinous material resulting from sugar and other organic compound degradation. Humins may also be produced by acid hydrolysis of carbohydrates. Yang and Sen [Chem. Sus. Chem., Vol. 3, pp. 597-603 (2010)] report the formation of humins during production of fuels from carbohydrates such as fructose, and speculate that the humins are formed by acid-catalyzed dehydration. The molecular weight of humins can range from 2.5 to 30 kDa.

As used herein, the term "miscible" refers to a mixture of components that, when combined, form a single phase (i.e., the mixture is "monophasic") under specified conditions (e.g., component concentrations, temperature).

As used herein, the term "immiscible" refers to a mixture of components that, when combined, form a two, or more, phases under specified conditions (e.g., component concentrations, temperature).

As used herein, the term "monophasic" refers to a reaction medium that includes only one liquid phase. Some examples are water, aqueous solutions, and solutions containing aqueous and organic solvents that are miscible with each other. The term "monophasic" can also be used to describe a method employing such a reaction medium.

As used herein, the term "biphasic" refers to a reaction medium that includes two immiscible liquid phases, for example, an aqueous phase and a water-immiscible organic solvent phase. The term "biphasic" can also be used to describe a method employing such a reaction medium.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry.

DETAILED DESCRIPTION OF THE INVENTION

The Figures described above and the written description of specific structures and functions below are not presented to limit the scope of what Applicants have invented or the scope of the appended claims. Rather, the Figures and written description are provided to teach any person skilled in the art to make and use the inventions for which patent protection is sought. Those skilled in the art will appreciate that not all features of a commercial embodiment of the inventions are described or shown for the sake of clarity and understanding. Persons of skill in this art will also appreciate that the development of an actual commercial embodiment incorporating aspects of the present inventions will require numerous implementation-specific decisions to achieve the developer's ultimate goal for the commercial embodiment. Such implementation-specific decisions may include, and likely are not limited to, compliance with system-related, business-related, government-related and other constraints, which may vary by specific implementation, location and from time to time. While a developer's efforts might be complex and time-consuming in an absolute sense, such efforts would be, nevertheless, a routine undertaking for those of skill in this art having benefit of this disclosure. It must be understood that the inventions disclosed and taught herein are susceptible to numerous and various modifications and alternative forms. Lastly, the use of a singular term, such as, but not limited to, "a," is not intended as limiting of the number of items. Also, the use of relational terms, such as, but not limited to, "top," "bottom," "left," "right," "upper," "lower," "down," "up," "side," and the like are used in the written description for clarity in specific reference to the Figures and are not intended to limit the scope of the invention or the appended claims.

Applicants have created methods and processes for the production of valuable organic products and alcohols from pentosan-comprising biomass materials using a closed-loop process having numerous advantages over prior production methods. For example, the controlled return of the slightly acidic aqueous stream following the dehydration of the $C_5$ carbohydrates extracted from the biomass allows for maintaining an optimized reaction process flow. Additionally, the method allows for increased amounts of both $C_5$-carbohydrate and $C_6$-carbohydrate-containing intermediate product steams to be efficiently separated and recovered and sent on to further upgrading and/or purification steps (dehydration, fermentation, etc), whereas often these intermediate products are lost or destroyed during treatment steps. Furthermore, the process methods allow for higher concentrations of pentosan-comprising biomass to be treated, which increased the product concentration, thereby reducing the size of equipment and facilitating the recovery of valuable intermediates and products overall. In addition, the use of extraction methods within the process allows for purification of the organic process stream without the inclusion of unwanted side-product impurities or humins, thus increasing the overall process production yield and making the process economically more attractive.

Figure 2:
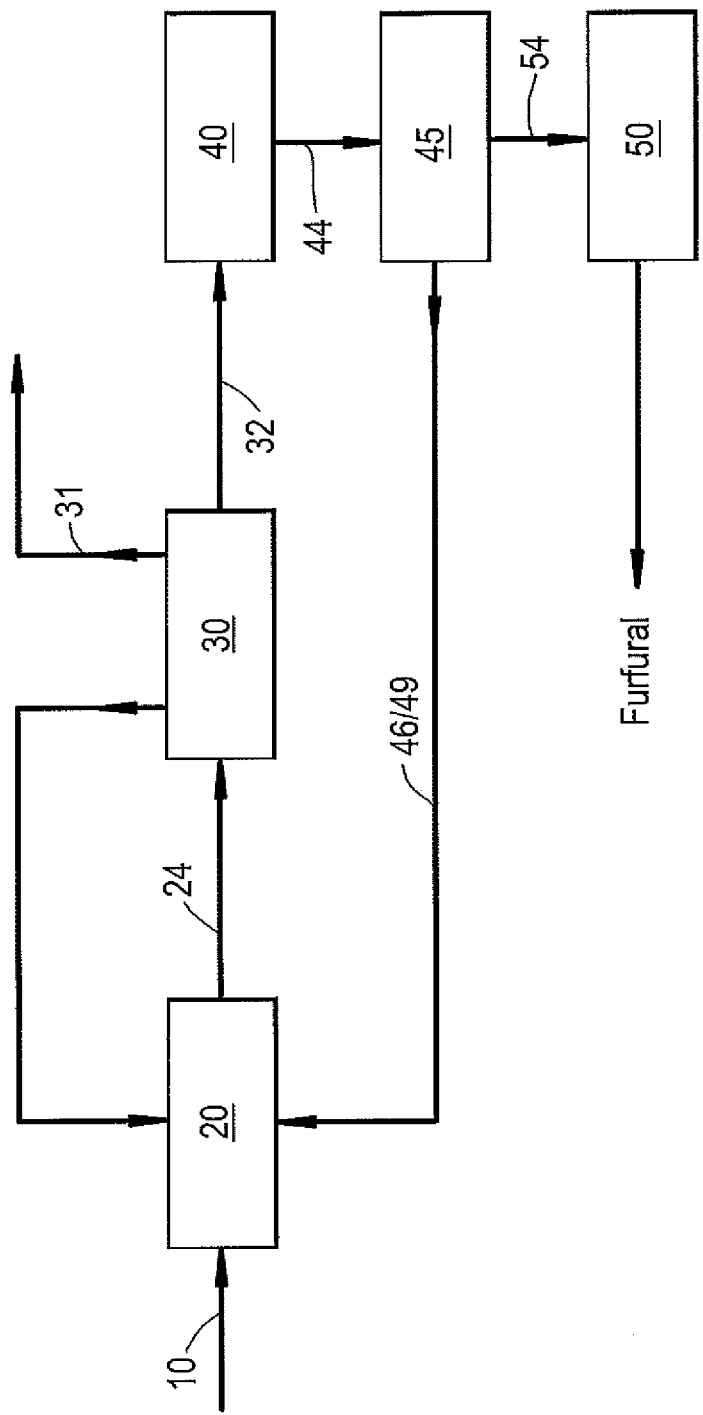
FIG. 2 illustrates a block flow diagram of the general steps of the closed-loop process of the present invention.
Figure 3:
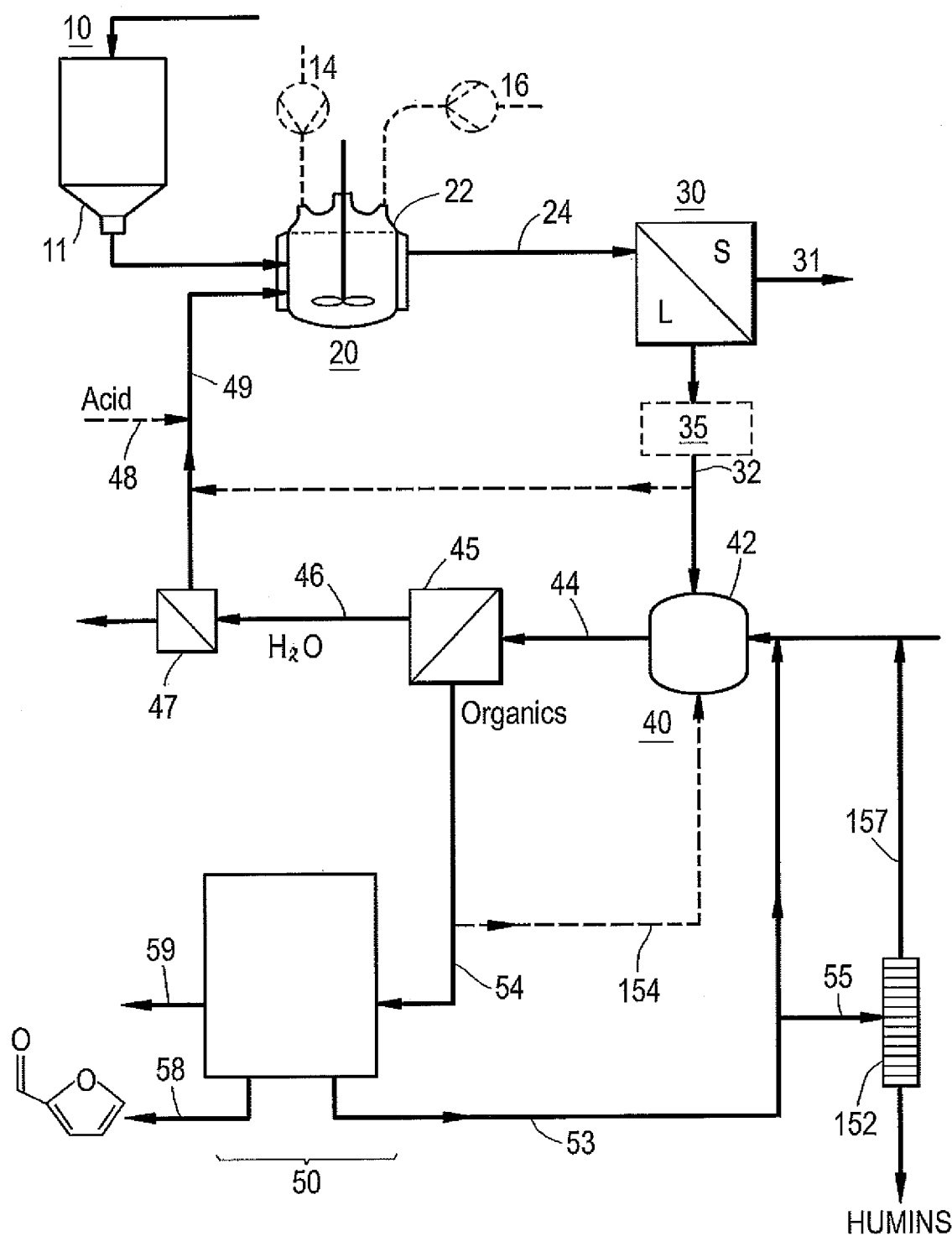
FIG. 3 illustrates a process flow diagram for an exemplary production process in accordance with select aspects of the present invention.

Turning now to the figures, FIG. 2 illustrates a general block flow diagram of an exemplary closed-loop process in accordance with the present invention. FIG. 3 illustrates a detailed process flow diagram for the process of FIG. 2. These figures will be described in conjunction with each other. As illustrated in the process flow diagram of FIG. 2, the closed loop process of the present disclosure includes a pentosan-comprising biomass processing or preprocessing/preparation step (not shown), followed by a digestion step 20, and thereafter the separation of the $C_5$-carbohydrate and solid product streams, the $C_5$-carbohydrate containing product stream proceeding to a dehydration step 40, and thereafter a liquid-liquid extraction step, the organic phase advancing to a separation zone, preferably comprising one or more distillation steps, 50 wherein furfural or other furan derivatives are isolated, while the liquid phase is metered back into the digestion step 20 so as to control the pH and the solids-to-liquids content within the digester and optimize the digestion process during a continuous loop production. The solid product stream may proceed to further process steps, such as to prepare chemical compounds like alcohols, to prepare pulp or to generate power.

More particularly, the general flow scheme of FIG. 2 illustrates an embodiment of the present invention for converting part of a biomass material into furfural in a primary reaction loop. A pentosan-containing biomass feedstock 10 is introduced into a digestion reaction system 20. The digestion reaction system 20 can comprise several components, including acid. The acid may be provided as fresh acid and/or as one or more aqueous acid recycle streams. A digested product stream 24 is obtained comprising digested biomass containing C5-carbohydrates, and solids comprising lignin, cellulose and hemicellulosic material. The digested product stream 24 is then introduced to a separation system 30, where a high solids/liquid mixture is separated to form a wet solid product stream 31, and the liquid product stream 32, which is directed to a dehydration system 40.

The wet solid product stream 31 contains at least 12 wt % of undissolved solids containing cellulose, preferably in the range of 15 wt % to about 40 wt % undissolved solids containing cellulose, preferably in the range of 15 wt % to 35 wt % undissolved solids containing cellulose, and more preferably in the range of 20 wt % to 25 wt % undissolved solids containing cellulose, based on the wet solid product stream.

The liquid product stream 32 comprises carbohydrate compounds, in particular the liquid product stream comprises $C_5$-carbohydrates, such as pentose. Liquid product stream 32 may optionally comprise $C_6$-carbohydrates such as hexose, however, the majority of the carbohydrates in the liquid product stream are $C_5$-carbohydrates, i.e. liquid product stream 32 comprises carbohydrate compounds, of which carbohydrate compounds at least 50 wt % are $C_5$-carbohydrate compounds, based on the total weight of the carbohydrate compounds in liquid product stream 32. The liquid product stream may comprise of up to 20 wt % to 95 wt % of the liquid contained in the digestion product stream.

The liquid product stream 32 is provided to a dehydration system 40 where the stream is subjected to dehydration reaction conditions, with the addition of acid and additional solvent as appropriate. At least a portion of the liquid product stream 32 is recycled to the digestion reaction system 20, where the liquid product stream 32 is recycled in such a manner as to keep the digestion reaction pumpable, preferably about 20 wt % or less of solids content in the digestion reactor 22. An advantage of recycling part of the liquid product stream 32 to digestion reaction system 20 is that the concentration of $C_5$-carbohydrates in liquid product stream 32 can be increased. Required make-up water can be introduced to the process system in numerous locations as appropriate to achieve desired results.

Dehydration system 40 is a biphasic system for performing a dehydration reaction. The use of a biphasic system compared to typical aqueous commercial processes for furfural production has the advantage that improved furfural yields may be obtained due to the in-situ extraction of furfural into the organic phase. Furthermore the use of an aqueous and organic phase allows for a more efficient separation of the furfural from the aqueous phase.

Dehydration process stream 44 is then introduced to a liquid-liquid extraction system 45. Aqueous recycle stream 46 (or explained herein below 49) is at least partly recycled to digestion reaction system 20. The organic liquid stream 54 is then introduced to a separation zone 50, preferably comprising one or more distillation units, so as to produce the desired product, furfural. Optionally, part of organic liquid stream 54 may be recycled to dehydration system 40. By recycling part of organic liquid stream 54 to dehydration system 40, the concentration of furfural in stream 54 may be increased which is beneficial when separating the furfural form the organic solvent. In accordance with embodiments of the invention, the solids containing cellulose in the wet solid product stream 31 (and products separated therefrom) can be separated out as pulp for use in the paper product industry, and can also be used to generate biomass-derived alcohols, see for instance US20120107887 incorporated herein by reference, biomass derived mono- and diacids, biomass-derived (polymeric) polyols, biomass-derived diols, power, and other chemicals useful in industrial manufacturing operations. As explained in more detail herein below, the solids containing cellulose may be used to from alcohols such as butanol/ethanol or butanediol, e.g. via hydrolysis and fermentation. Glycols like ethylene glycol and propylene glycol may be produced via hydrolysis of the C6 sugars, but may alternatively be produced by a catalytic conversion of the C6 sugars to diols, see for instance US20100019191 incorporated herein by reference. The cellulose can also be converted to mono- and diacids such as acetic acid, lactic acid, levulinic acid or succinic acid by means of fermentation or chemical conversion.

The wet solid product stream can suitably be used to generate power by burning the wet solid residue e.g. in a in co-generation boiler. Alternatively, the wet solid product stream may be converted and optionally dried to form pellets, which can be used to produce for instance power at remote locations.

Exemplary biomass-derived diols include, but are not limited to, $C_2$-$C_{10}$ diols such as ethylene glycol, propylene glycol, 1,4-butane diol (BDO), pentane diol, propylene glycol, 1,2-propanediol, 1,3-propanediol, 1,5-pentanediol, 1,4-pentanediol, 1,2-butanediol, 1,3-butanediol, 2,3-butanediol, 1,4-butanediol 1,2-pentanediol, 1,3-pentanediol, 1,4-pentanediol, 1,5-pentanediol, 2,3-pentanediol, 2,4-pentanediol, and combinations thereof.

Exemplary chemicals that can be produced from the production steps detailed herein include butanol (both n-butanol and iso-butanol), butanol mixes, HMF (hydroxymethyl) furfural and MMF (5-methoxymethyl furfural).

Additionally, the solids removed during various steps of the closed-loop process described herein can be converted to power or energy, such as by burning or otherwise treating the solids in a power plant or similar power production facility, the power being storable for later sale, or used to fuel the closed-loop process, thereby increasing the process efficiency. The solid tar and/or humins can also be converted to a fuel gas, such as by gasification methods to produce low tar fuel gas with low emissions and no toxic waste streams or burned as fuel in a boiler.

Biomass Processing

With reference to FIG. 3, the pentosan-containing biomass material 10 (shown in biomass container 11) can be used in a wet, dry or substantially dry form, and introduced directly into a digestion vessel 22 (also referred to herein as a digester), and may be pre-ground or not. For example, the pentosan-containing biomass material used can be sized by grinding to a desired particle size prior to introduction to the digester 22. In a non-limiting example, the biomass can be ground to a particle size in the range of about 0.1 mm to about 10.0 mm, about 0.1 mm to about 5.0 mm, or about 0.1 mm to about 2.0 mm. In the instance that the biomass is ground and/or sized to a specific particle size, the particle size can be selected such that the digestion process occurs with the highest efficiency.

The pentosan-containing biomass material 10, whether ground or not, can also be mixed with water to form a slurry of a desired consistency prior to introducing the biomass to the digester 22. For example, the slurry can be in the range of from about 5% solids to about 100% solids by weight, e.g., about 20%, about 30%, about 40%, about 50%, about 60%, about 70%, about 80%, about 90%, or about 100% solids by weight, as well as slurry concentrations within these ranges, e.g., about 25% by weight, or about 5% by weight.

In accordance with select aspects of the present invention, the pentosan-containing biomass material 10 that is advanced to the digester 22 may further include or be mixed with an aqueous liquid (water) or liquids from other, downstream steps in the process, such as fluid stream 49 which may optionally contain acids from the process, or by an addition step prior to re-introduction into the digester. The pentosan-containing biomass material 10 may optionally also be separated into a liquid phase and a solids phase using any suitable separation method, including centrifugation, decanting, filtration and flocculation, so as to dilute or adjust the biomass in the initial steps of the process to optimize production.

The pentosan-containing biomass material 10 suitable for use herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks and corn stover, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. The term "biomass" includes virgin biomass and/or non-virgin biomass such as agricultural biomass (such as grains, e.g., corn, wheat and barley; sugarcane; cone stover, corn cobs and other inedible waste parts of food plants; grasses such as switchgrass), forestry biomass (such as wood and waste wood products), commercial organics, construction and demolition debris, municipal solid waste, waste paper, and yard waste.

In accordance with a non-limiting aspect of the invention, the biomass is a lignocellulosic material such as bagasse comprising from about 30 wt % to about 50 wt % cellulose, from about 15 wt % to about 40 wt % hemicellulose (including xylose), from about 10 wt % to about 25 wt % total lignin (including both acid insoluble and acid soluble lignins), and an ash content ranging from about 1 wt % to about 10 wt %.

Digestion

As shown in FIG. 3, in the next step of the production process, the pentosan-containing biomass is subjected to a digestion in digester step 20. The pentosan-containing biomass material 10 is introduced from container 11 into a digester 22, using any suitable introducing methods, such as via a screw extruder or by way of a material addition pipe stream.

In the digestion step 20, the biomass is either admixed with an aqueous liquid (e.g., water) to a target solid-to-liquid (S:L) concentration, or if already in slurry form, adjusted to the appropriate concentration ratio. The solid to liquid weight ratio within the digester 22 preferably ranges from about 1:3 to 1:30, preferably about 1:3 to about 1:15, more preferably from about 1:6 to about 1:15, still more preferably from about 1:6 to about 1:10, even still more preferably from about 1:8 to about 1:10. The digestion process step is carried out at an elevated temperature, preferably above about 100° C., including in the range from about 100° C. to about 250° C., and from about 110° C. to about 160° C., for a period of time ranging from about 1 minute to about 8 hours (hrs), preferably from about 0.5 hrs to about 4 hrs. The pentosan-containing biomass may preferably be admixed with at least part of liquid stream 32 and/or at least part of aqueous recycle stream 46, described in more detail herein below, so as to maintain a consistency in the digester.

The digestion step also includes the addition of one or more acids, or buffer solutions, to the digester 22 via acid stream 16, so as to adjust the pH of the digestion reaction and maintain it with a selected pH range. Preferably, the pH is less than about pH 5, more preferably less than about pH 3, and most preferably less than about pH 1. Preferably, a pH range is used in the range of from 0 to 5, more preferably of from 0 to 4, even more preferably of from 0 to 3, still more preferably of from 0 to 2. Any suitable digester equipment known in the art may be used.

In accordance with preferred aspects of the invention, the acid catalyst introduced into the digester is introduced by an acid stream 16, by way of an aqueous process loop recycle stream 49, or both, and is introduced in amounts and at a rate so as to optimize the digestion process. The acid catalyst is preferably an inorganic acid, most preferably a mineral acid such as HCl, HNO$_3$, H$_2$SO$_4$, H$_3$PO$_4$, H$_3$BO$_3$, and the like. Organic acids e.g., acetic acid, formic acid, oxalic acid, levulinic acid, toluene sulfonic acid, citric acid, etc. may also be used. The acid may be provided as such or as part of one or more of the streams provided to the process. In one particular example, some types of biomass that may be used as the starting material intrinsically contain acids or will form acids upon being subjected to the digestion, examples of such acids intrinsically contained or formed include, but are not limited to, formic acid or acetic acid. When using such types of biomass, the need to add acid may reduce or even eliminate as the in-situ generated acid will provide the necessary acidic pH.

The amount of acid to be added, or the amount present within the digestion slurry, is preferably adjusted to be in the range from about 0.1 wt % to about 10 wt % acid.

Alternatively, a basic, preferably caustic pretreatment could be used instead of the acid pretreatment, this would however require a subsequent treatment to lower the pH of the aqueous C5 sugar feed stream prior to the conversion of the C5 sugar.

Separation

With continued reference to FIG. 3, once the digestion process is complete, the digestion process stream 24 is transferred to a solid-liquid separator 30 or phase separator, where the solid product stream 31 comprising solids, and primarily solids comprising cellulose, is separated from the liquid product stream 32 that contains primarily C$_5$-carbohydrate products, such as xylose. The liquid product stream 32 is subsequently provided to a dehydration step 40 for dehydration of the C$_5$-carbohydrates in the bulk liquid product stream, by feeding stream 32 into a reaction vessel 42 of dehydration step 40.

Either one or both of streams 24 or 32 may be flashed to remove part of the water (not shown) to concentrate streams 24 and/or 32. In the non-limiting embodiment shown m in FIG. 3, stream 32 is flashed in flash vessel 35.

The separation step in solid/liquid separator 30 can be carried out in any suitable solid/liquid separating device such as, but not limited to, filters, centrifuges, screw presses, etc. As mentioned before, the liquid stream may optionally be recycled to the digester to build the concentration of C$_5$-carbohydrates. Optionally, stream 32 can also be subjected to a flash, distillation or multi-effect evaporator to increase the C$_5$-carbohydrate concentration.

Dehydration

The dehydration step 40 occurs in a biphasic mixture of aqueous and organic phases, the aqueous phase being that carried through from separation step 30, the organic phase being one or more organic solvents that are substantially immiscible with the aqueous phase. The use of organic solvent with preferred selectivity towards furfural extraction, extracts furfural from the aqueous phase as it is formed during the dehydration reaction. This may improve overall furfural yield. A further advantage is that by extracting the furfural into the organic phase, the undesired loss of furfural via degradation reactions happening in the aqueous phase is reduced.

The preferred organic phase for use in the present invention comprises a water-immiscible organic solvent that is substantially immiscible with the aqueous phase containing C$_5$-carbohydrate products. Preferably such water-immiscible organic solvents have a maximum water solubility of less than about 30 wt %, preferably less than about 10 wt %, and most preferably less than about 2 wt % at ambient (room) temperature. The preferred organic solvents are 1-butanol, sec-butyl phenol (SBP), MIBK, toluene and dichloromethane (DCM). Other organic phases, especially other alcohols, ketones, and halogenated alkanes, may also be utilized. Thus, for example, organic solvents such as straight or branched alcohols (e.g. pentanol, tertbutyl alcohol, etc.), cyclic alcohols (e.g., cyclohexanol), straight or branched alkanones (e.g. butanone (i.e., methylethyl ketone (MEK)), pentanone, hexanone, heptanone, diisobutylketone, 3-methyl-2-butanone, 5-methyl-3-heptanone, etc.), and cycloalkanones (e.g., cyclobutanone, cyclopentanone, cyclohexanone, etc.) may be used in the present invention. Aliphatic and cycloaliphatic ethers (e.g., dichloroethylether, dimethyl ether, MeTHF), saturated and unsaturated aliphatic or aromatic hydrocarbons (decane, toluene, benzene, cymene, 1-methyl naphthalene), oxygenated hydrocarbons (e.g. furan, nonyl phenol, etc.), and nitroalkanes (e.g., nitromethane, nitropropane, etc.) may also be used. Likewise, halogenated derivatives of the above-noted compounds, as well as other halogenated alkanes may also be used as the organic phase (e.g., chloromethane, trichloromethane, trichloroethane, and the like). Lignin derived solvents such as Guaiacol, Eugenol, 2-Methoxy-4-propylphenol (MPP), 2-Methoxy-4MethylPhenol (MMP) or mixture thereof may also be used. Combination of solvents can also be used to fine tune the extracting capability of the solvent may also be used.

Preferably, the organic solvent or the combination of organic solvents can extract 80 mol % or more of the furfural produced from the aqueous phase, while at the same time dissolve less than 1 wt %, more preferably less than 0.1 wt %, more preferably less than 0.01 wt % of water, based on the organic solvent.

The weight percentage of organic phase material is in a range suitable to create a biphasic system with the aqueous phase, e.g., from about 5% by weight to about 95% by weight, based on the combined weight of the aqueous phase and organic phase.

The dehydration process step 40 is carried out for a period of time ranging from about 1 minute to about 24 hrs, preferably for a period of time ranging of from about 5 minutes to about 12 hrs, more preferably from about 10 minutes to about 6 hours, still more preferably 30 minutes to 4 hrs., even still more preferably 30 minutes to 2 hrs. or for times within these ranges, at an elevated temperature above about 100° C., including in the range from about 100° C. to about 250° C., from about 110° C. to 200° C. and from about 140° C. to about 180° C. One or more acids as described above may be added in order to catalyze the reaction process, preferably mineral acids such as H$_2$SO$_4$, HCl, and the like.

The concentration of the C$_5$-carbohydrate compounds in the dehydration reactor 42 can vary depending upon the product to be obtained. However, in accordance with aspects of the present invention, it has been found that the reaction is optimized for obtaining furfural or other furan derivatives when the concentration of C$_5$ components during the dehydration process step 40 is between about 0.1 wt % and 20 wt %, more preferably between about 0.2 wt % and 10 wt %, inclusive %, based on the weight of the aqueous phase. During the dehydration process step, at least part, and preferably substantially all, of the C$_5$-carbohydrate compounds are converted to furfural. Optionally, other furan derivatives may also be formed. Due to the nature of the furfural, and optional other furan derivatives, the furfural preferably resides in the organic phase of the biphasic mixture.

Due to the preference of the formed furfural to reside in the organic phase in rather than in the aqueous phase at least part of the formed furfural, and preferably more than 50 wt %, still more preferably 75 wt % of the formed furfural will dissolve in the organic phase.

Product Recovery

Following the dehydration step 40, dehydration product stream 44 is transferred to a liquid-liquid extractor 45 for the extraction step, optionally after cooling of the stream. The dehydration product comprises at least part of the biphasic mixture, comprising an aqueous phase and a water-immiscible organic phase that was present in the reaction vessel during the dehydration process and thus comprises water, organic solvent and further comprises furfural that was formed by the dehydration of the $C_5$-carbohydrates. The furfural, herein will be predominantly dissolved in the organic solvent.

The extractor 45 can be operated at a temperature range from about room temperature to about the dehydration temperature, so long as the liquid separates into two liquid phases at the extractor temperature. The organic phase is separated from the aqueous phase, and thus obtained aqueous recycle stream 46 may be fed directly back into the process loop at the digestion stage. The aqueous recycle stream 46 will comprise the acid catalyst. Depending upon the salt, and optional other organic byproduct, content of the aqueous stream, aqueous recycle stream 46 may be treated to remove unwanted or excessive amounts of salts and/or organic byproducts. Preferably, aqueous recycle stream is subjected to a separation step 47. The recovered aqueous recycle stream 49 obtained after treatment of aqueous recycle stream 46, is reintroduced to the digester 22. Salts, and optionally other organic byproducts like humins, are formed as a byproduct during one or more of the process steps. Typically, part of stream 46 may also be purged from the process to prevent the build-up of byproducts as part of separation step 47. Depending upon the pH or water content of aqueous stream 49, acid 48 may optionally be added prior to its addition to the digester 22 in order to maintain overall reaction pH and reaction kinetics.

Prior to undergoing the liquid-liquid extraction step, dehydration product stream 44 may optionally be routed through a, preferably solid/liquid, separation step, to remove any insoluble humins or other tar that may have been formed during the dehydration step 40, and which may otherwise negatively interfere with the separation of the organic phase from the aqueous phase, or later separation or purification steps (not shown). The humins or tar will predominantly end up in the solid phase and will thus not, or to a lesser extent, affect the subsequent organic/aqueous separation step 45. Formation of tar, char, and/or humins is a well-known problem associated with the production of bio-based products, and their non removal from the production stream can result in problems during downstream purification and/or separation steps.

The organic phase, i.e. the organic solvent, is retrieved from extraction step 45 as organic product stream 54, containing the target organic compounds such as furfural and optionally furan derivatives such as furfural precursors (THF, furan, 2-methyl THF). Although, part of organic product stream 54 may be recycled to dehydration reactor 42, the majority of organic product stream 54 is subjected to a separation step, preferably one or more distillation steps, in separation zone 50. Residual water from the reaction that was not removed during the liquid-liquid extraction step, and which may contain acetic acid or other water-soluble impurities, is removed via flow stream 59 from separation zone 50, with recovery of furfural via stream 58.

Organic solvents 53 removed/recovered during the separation in separation zone 50 step can be recycled back into the process, such as by reintroduction back into the dehydration reaction vessel 42, in order to minimize production costs and maintain the reaction process and process efficiency. Alternatively, at least part of the organic solvent stream 53 can be directed via stream 55 to a further solvent purification process 152 such as column distillation/separation or solvent-solvent extraction, prior to reintroduction back into the production process, so as to remove impurities, primarily humins (heavy byproducts), as well as purify the solvent before reintroduction. As also shown in the scheme, after the solvent purification step 152, fresh solvent may be added to the purified solvent stream 157 prior to reintroduction to the dehydration reaction vessel 42 so as to maintain the required volume of organic phase in the dehydration step.

Solid product stream 31 may still contain substantial amounts of residual $C_5$-carbohydrates. In order to extract any residual C5 carbohydrates, the solids are preferably, washed with at least part of aqueous stream 46 or 49 (not shown) prior to providing stream 46 or 49 to digester 22.

In a particular embodiment of the process according to the invention the solid product stream 31 may be further treated to produce alcohols and glycols. The solids comprising cellulose contained in solid product stream 31, once separated from the $C_5$-carbohydrate-containing liquid process stream 32 as discussed in detail above, can be subjected to a variety of processes. The subsequent processing of the solids includes being subjected to enzymatic hydrolysis for conversion to fermentable sugars by introduction into a hydrolysis reactor to undergo a hydrolysis, and thereafter being subjected to one or more fermentation steps. During, or prior to the introduction of the solid product stream to the hydrolysis, the solid product stream can be diluted with an aqueous liquid and optionally pretreated as appropriate to render the process stream more susceptible to hydrolysis.

Hydrolysis

Before and/or simultaneously with fermentation, the solids in the solid product stream 31 are enzymatically hydrolyzed to break down cellulose into sugars and/or oligosaccharides. The hydrolysis can be continuous or semi-continuous, and may be carried out in a single stage, in two stages, or in multiple stages in a semi-continuous or continuous manner.

In practice, the hydrolysis is carried out in a hydrolysis system, which may include a single hydrolysis reactor or a series of hydrolysis reactors. The number of hydrolysis reactors in the system depends upon the cost of the reactors, the volume of the aqueous slurry being fed to the reactor, and other factors. For typical commercial-scale production facilities, the typical number of hydrolysis reactors may be from 1 to 10, more preferably from 2 to 6, or any number there between. In order to maintain the desired hydrolysis temperature, the hydrolysis reactors may be jacketed with steam, hot water, or other suitable heat sources. Preferably, in accordance with aspects of the present invention, the hydrolysis of the cellulose in stream 31 is a continuous process, with continuous feeding of the solid product stream 31 and withdrawal of the hydrolysate slurry. However, it should be understood that batch processes are also included within the scope of the present invention. In accordance with a further embodiment of the invention, a series of Continuous Stirred-Tank Reactors (CSTR) may be used for a continuous process; in accordance with another embodiment, Short Contact-Time Reactors (SCTR) along with a finishing reactor may be used. A thinning reactor may also be included within the hydrolysis system, as appropriate.

The hydrolyzate may in one embodiment be separated again into a solids-containing phase and a liquid phase, and the hydrolyzate in the liquid phase can further undergo a fermentation process to produce a fermentation product, such as one or more alcohols/diols/acids, as discussed in detail below. The solids phase from the separation of the hydrolyzate liquid stream may be further processed, reintroduced into selected sections of the overall process, or removed and disposed of (if the primary contents are water and humins). It is contemplated that the hydrolysis and fermentation may be carried out simultaneously or sequentially.

Fermentation

According to embodiments of the invention, the hydrolyzed predominantly $C_6$-carbohydrate containing material is then introduced into one or more fermentation tanks, vessels, or reactors, and is thereafter fermented by at least one fermenting microorganism capable of fermenting fermentable sugars, such as glucose, xylose, mannose, and galactose directly or indirectly into a desired fermentation product, such as a fermentation broth containing an alcohol fermentation product. As indicated herein, owing to the closed-loop nature of the instant process and the removal of a majority of the $C_5$-carbohydrate components, there is primarily only glucose present for the fermentation, which in turn allows for the use of robust wild yeast fermentation microorganisms, versus the more sensitive genetically-modified (GM) fermentation organisms needed when a mixture of $C_5$-carbohydrate and $C_6$-carbohydrate components are fermented. Additionally, the water/acid recycle stream 49 (and its related recycle streams) can be tuned so as to minimize the concentration of acetates or furans in the hydrolysate, which are known inhibitors for fermentation organisms. Thus, the fermentation proceeds in a more rapid and robust manner than typically experienced.

The fermentation is preferably ongoing for between 8 to 96 hours, preferably 12 to 72, more preferable from 24 to 48 hours. In an embodiment the fermentation is carried out at a temperature ranging between about 20° C. and about 50° C., preferably from about 26° C. to about 34° C. In an embodiment, the pH of the fermentation process is from pH 3 to 6, preferably around pH 4 to 5, which is maintained by the addition of suitable acids or bases via pH control line 73.

Preferred for alcohol production, especially ethanol and similar alcohol fermentation products, is yeast of the species *Saccharomyces cerevisiae*, preferably strains which are resistant towards high levels of ethanol, i.e., up to, e.g., about 10, 12 or 15 vol. % ethanol or more, such as 20 vol. % ethanol. The process of the invention may be used for producing any suitable fermentation product from the $C_6$-carbohydrate stream. Especially contemplated fermentation products include alcohols (e.g., ethanol, methanol, n- and i-butanol, and 1,4-butane diol (1,4-BDO), 2,3-butanediol, and 1,3-propanediol); organic acids (e.g., citric acid, acetic acid, itaconic acid, lactic acid, gluconic acid, succinic acid, and 3-hydroxypropionic acid); ketones (e.g., acetone). Particularly contemplated products include consumable petroleum industry products, e.g., ethanol and modified straight chain alcohols. In a preferred embodiment the fermentation product is an alcohol or diol, especially 1,4-BDO or ethanol. The fermentation product, such as ethanol, obtained according to the invention, may preferably be fuel alcohol/ethanol.

It should be appreciated by those of skill in the art that the techniques disclosed in the examples which follow represent techniques discovered by the inventors to function well in the practice of the inventions, and thus can be considered to constitute preferred modes for its practice. However, those of skill in the art should, in light of the present disclosure, appreciate that many changes can be made in the specific embodiments which are disclosed and still obtain a like or similar result without departing from the scope of the inventions.

EXAMPLES

The following examples are included to demonstrate preferred embodiments of the inventions.

General Methods and Materials

Digestion

Digestions were carried out in a 500 ml zipperclave reactor (Autoclave Engineers, Inc.) and/or a 300 ml Parr autoclave. Biomass (eg. Bagasse) was weighed and placed in the reactor. The composition of the biomass (bagasse) charged is given in Table 1. After the reaction was complete the aqueous liquid phase was separated from the treated product mixture using a filtration apparatus using house vacuum system. The content of the aqueous liquid phase is analyzed for carbohydrate composition. The residual biomass is used for solids analysis. Compositional analysis of the residual biomass is carried out to determine the carbohydrate and lignin content.

Biphasic Dehydration

Biphasic acid dehydration of C5 carbohydrates (primarily xylose) containing aqueous liquid stream was carried out in a 500 ml zipperclave reactor (Autoclave Engineers, Inc.) and/or a 300 ml Parr autoclave. In a typical run, acidified C5 carbohydrate feed aqueous stream was added to the reactor along with an immiscible organic solvent with a certain Aqueous: Organic ratio on weight basis. The reactor is then heated to the reaction temperature and held at that temperature for the residence time indicated in the examples. After the reaction was complete the reaction mixtures were weighed and transferred into a separatory funnel to allow for two liquid phases to separate. After separation, each phase was weighed and analyzed for its content. The aqueous phase was analyzed using HPLC and the organic phase was analyzed using GC as described below.

Analytical Methods

Solids compositional analysis of the feedstock the digested biomass samples were conducted using standard TAPPI (T-222, T-211, T-249) methods.

The aqueous phases from digestion and dehydration runs were analyzed and quantified for various components such as glucose, xylose, arabinose, mannose, formic acid, acetic acid, levulinic acid, furfural using high-performance liquid chromatography (HPLC) system (Shimadzu) equipped with a refractive index detector (Shimadzu) on a BIO-RAD 87H Column. Prior to injection, the samples were filtered through 0.45 μm HV filters (Millipore, Bedford, Mass., USA), and a volume of 10 μL was injected. The mobile phase for the column was 5 mM $H_2SO_4$ in Milli-Q water at a flow rate of 0.6 mL/min.

In a typical biphasic dehydration run the furfural concentration in the organic phase or layer was measured using gas chromatography (GC). Agilent 6890 GC with a DB-1301 capillary column installed in its split/splitless inlet was used with the FID. The column parameters were 30 m length, 0.25 mm ID, and 1.0 μm film thickness. Method parameters were as follows:

Oven Temp Program: 40° C. Hold 3 min, Ramp 10° C./min to 280° C., Hold 3 min.

Inlet Temp 250° C., Injection Volume 1.0 µl, Split ratio 100:1, Constant Pressure 20 psi Helium Carrier gas, Detector Temp 325° C., $H_2$ flow 35 ml/min, Air 400 ml/min, and Helium Makeup 25 ml/min.

Calculations

Solids dissolved was calculated as weight percentage ratio of oven dried digested biomass material to the total amount of feed (on dry basis).

Xylan recovery accounts for how much xylan is removed during digestion in the form of xylose and furfural.

Xylan Recovery={132/150*[Xylose]$_w$+132/96*[FUR]$_w$}/[Xylan]$_{feed}$

Furfural (FUR) formation ratio indicates how much of xylan is in the form of furfural at digestion conditions. This ratio should be low for an effective digestion process.

FUR/(FUR+Xylose) ratio=150/96*[FUR]$_w$/{150/96*[FUR]$_w$+[Xylose]$_w$}

Xylose Conversion={[mole of Xylose]$_{feed}$-[mole of Xylose]$_{AP}$}/[mole of Xylose]$_{feed}$ Furfural Selectivity={[moles of FUR]$_{AP}$+[moles of FUR]$_{OL}$}/{[mole of Xylose]$_{feed}$-[mole of Xylose]$_{AP}$}

The subscript "w" refers to the basis being weight.

The subscript "AP" refers to aqueous phase.

Biomass Composition

In table 1, the composition of the biomass used in the examples is shown. For hemicellulose and lignin a further division into the separate components is also provided in table 1.

TABLE 1

Biomass (Bagasse) composition used
Bagasse composition (wt % on dry basis)

| Cellulose | 40 | |
| --- | --- | --- |
| Hemicellulose | 28.5 | |
| Glucoronic Acid | | 0.7 |
| Xylose | | 22.8 |
| Arabinose | | 2.2 |
| Acetic Acid | | 3.9 |
| Total Ligin | 18 | |
| Acid Insoluble Lignin | | 16.75 |
| Acid Soluble Lignin | | 1.25 |
| Total Ash | 3.5 | |
| Extractives (Ethanol) | 9.75 | |
| Total | 99.75 | |

Example 1

Digestion of Biomass to Extract Xylan in the Form of Xylose and Furfural

For each run, biomass was charged into a batch reaction vessel described above at a selected biomass: water (S:L) ratio and stirred. The reactions were performed for a certain period of time, given acid concentration and temperature as indicated in the Table 2. The reaction mixture was then filtered and the filtrate collected and analyzed via HPLC for xylan recovery (includes xylose and furfural formed). The solid was washed with water, filtered and dried to measure amount of dissolved solids. The wet solids were washed with water, and the wet cake dried in a drying oven equipped with a vacuum trap (to collect solvent and/or water), and analyzed for content.

TABLE 2

Summary of Data for Biomass Digestion.

| Run | S:L weight ratio | $H_2SO_4$ (wt %) | Temp (° C.) | Time (h) | Solids\ Dissolved (wt %) | Xylan Recovery (Xylose + FUR*) (wt %) | FUR*/(FUR* + Xylose) weight ratio |
| --- | --- | --- | --- | --- | --- | --- | --- |
| 1 | 1:10 | 4 | 120 | 1 | 35 | 84 | 9 |
| 2 | 1:10 | 1 | 120 | 4 | 32 | 84 | 7 |
| 3 | 1:10 | 1 | 140 | 3 | 39 | 80 | 31 |
| 4 | 1:8 | 1 | 130 | 3 | 59 | 80 | 13 |
| 5 | 1:8 | 1 | 140 | 3 | 64 | 78 | 29 |
| 6 | 1:8 | 1 | 150 | 2 | 38 | 71 | 42 |
| 7 | 1:8 | 1 | 160 | 1 | 43 | 76 | 35 |

FUR = furfural

From the experiments shown above, a lower solids-to-liquid (S:L) ratio leads to accelerated dissolution/degradation. Additionally, about 80-85% xylan can be recovered with 7-10% degradation to furfural at 120° C. over a 4-hour reaction time at 1 wt % acid concentration or at a lower residence time of 1 h with higher acid concentration (4 wt %).

Example 2

Solvent Screening Runs for Furfural Production

Figure 4:
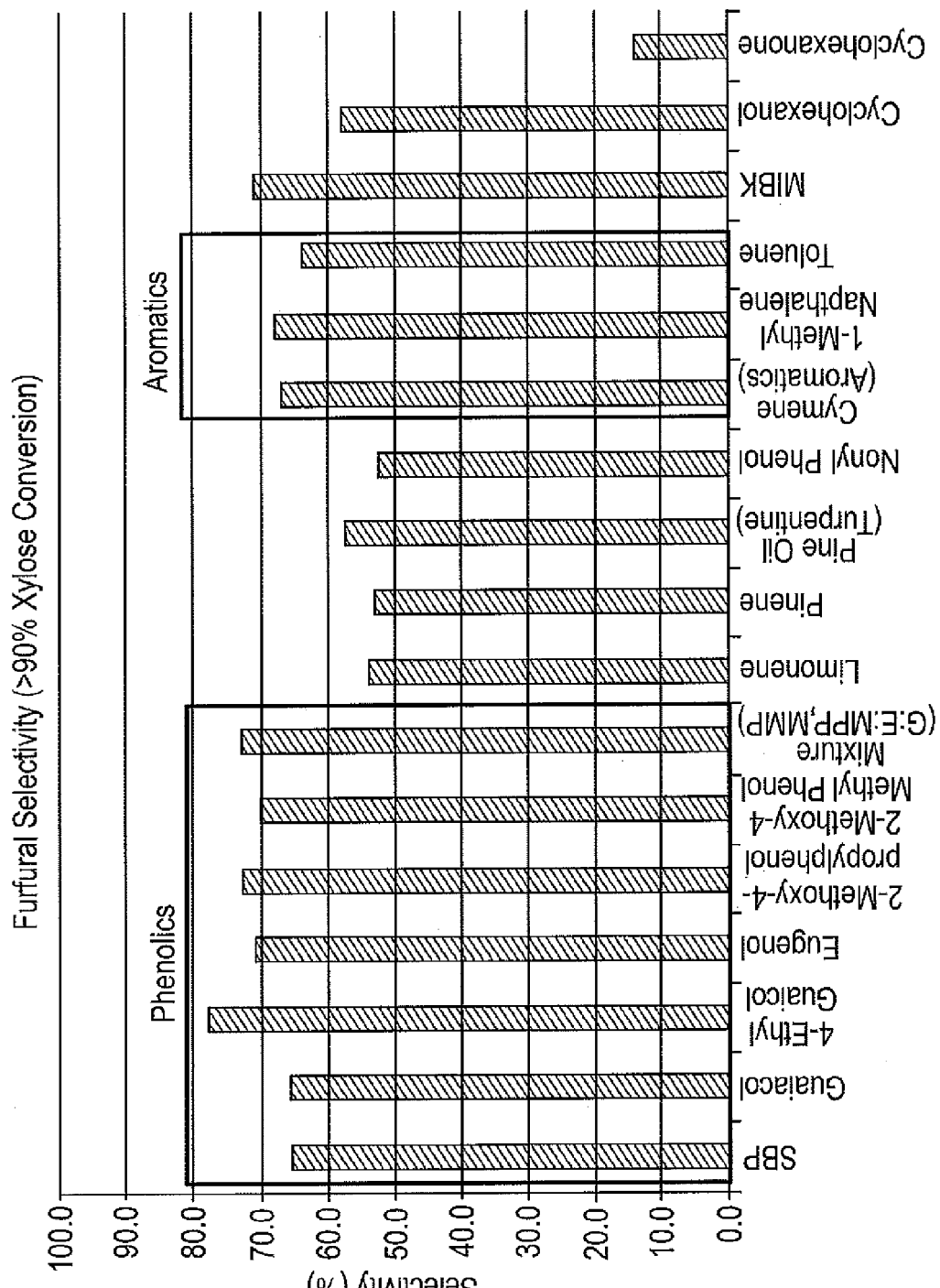
FIG. 4 illustrates the furfural selectivity from xylose for various solvents in a biphasic acid dehydration reaction system.

Various different solvents were screened for xylose selectivity towards furfural. In a typical run, 100 g of 5 wt % xylose solution (which can be assumed to be produced via various digestion runs) is prepared with 1 wt % $H_2SO_4$ acid concentration. Equal amounts (100 g) of immiscible organic solvent is added to the reactor to create a biphasic reaction medium. The reactor was then heated to 170° C. and the temperature was held for a total time of 1 h from heating. In all cases, conversion of xylose was more than 90% with the selectivity towards furfural as indicated in FIG. 4, which shows the furfural selectivity from xylose for various solvents in a biphasic acid dehydration reaction system.

The results shows various different kind of solvents can be used for furfural production based on ease of separation of furfural from the solvent and solvent losses encountered in overall process scheme.

Example 3

Furfural Extraction with Various Solvents

The liquid-liquid extraction experiments were conducted wherein an aqueous mixture (representative of final reaction mixture) was prepared as indicated in Table 3 was mixed with an equal amount of immiscible organic solvent. The mixture was stirred for 15 minutes at room temperature. After mixing, the mixture was separated in a separatory funnel into aqueous phase and an organic phase. The aqueous phase was analyzed for xylose, acetic acid, formic acid, furfural using HPLC and organic phase was analyzed for furfural. The difference in the amount of acetic and formic acid charged vs measured in the aqueous phase was assumed to present in the organic phase. Table 4 shows how much (mol %) of compound was transferred to the organic phase.

TABLE 3

Aqueous Feed Mixture for liquid-liquid extraction experiments

| Component | Content (wt %) |
|---|---|
| Xylose | 0.50 |
| Furfural | 3.00 |
| Acetic Acid | 1.00 |
| Formic Acid | 0.50 |
| Water | 95.0 |

TABLE 4

Solvent's extracting capability for furfural, acetic and formic acid from the aqueous stream.

| | Content in the organic phase (% mol) | | |
|---|---|---|---|
| | Furfural | Acetic Acid | Formic Acid |
| Sec-ButylPhenol (SBP) | 98% | 33% | 16% |
| Methyl IsoButyl Ketone | 92% | 40% | 41% |
| Cyclohexanone | 92% | 55% | 60% |
| Cyclohexanol | 83% | 60% | 55% |
| Toluene | 85% | NA | NA |
| Guaiacol (G) | 95% | 29% | 17% |
| 4-Ethyl Guaicol | 94% | 22% | 13% |
| Eugenol (E) | 93% | 19% | 10% |
| 2-Methoxy-4-propylphenol (MPP) | 93% | 22% | 15% |
| 2-Methoxy-4MethylPhenol (MMP) | 92% | 18% | 12% |
| Equal Mixture (G:E:MPP:MMP) | 94% | 22% | 13% |
| Limonene | 56% | 2% | 3% |
| Pinene | 40% | 1% | 1% |
| Pine Oil | 43% | 2% | 2% |
| Nonyl Phenol | 95% | 23% | 10% |
| Cymene | 73% | 8% | 7% |
| 1-Methyl Napthalene | 84% | 8% | 8% |

For a good solvent it is not only important to have high selectivity towards furfural but it should also extract most of furfural produced from the aqueous phase while extracting minimal of other byproducts such as acetic acid, formic acid and water carry over in the organic phase. Phenolic solvents have high extracting power for solvent (>90 mol %) but they also extract quite a bit of acetic/formic acid (>10 mol %), whereas aromatic solvents such as Cymene, 1 methyl naphthalene have slightly lower furfural extracting power (>75 mol %) but they also extract much lower acetic/formic acid (<10 mol %).

Example 4

Furfural Formation Using Multiple Recycles to Demonstrate Closed Loop Concept for Recycling Water and Acid Acid digestion: Into a 500 mL Hastelloy Zipperclave batch reactor containing 300 g of a 1% $H_2SO_4$ aqueous acid solution in water was added 30 g bagasse, the reactor was heated to 120° C., and the digestion reaction was conducted for a period of 4 hours. The reactor was allowed to cool, and the contents (a slurry) were filtered to collect the filtrate; the collected wet solids were weighed and set aside. The wet solids were washed with 300 g fresh water, and the wash water from the first cycle set aside for further analysis. An analytical sample of the filtrate was analyzed by HPLC, and the collected filtrate (approx. 250 mL) was recycled into the reactor and fresh 1% $H_2SO_4$ (aq. solution) was added to the reactor to bring the total weight of the contents of the reactor to 300 g. Fresh bagasse (30 g) was added to the reactor containing the aqueous acidic solution and the collected filtrate from the first reaction cycle, and the digestion process repeated (120° C. for 4 hr). This recycle of the digestion process step was repeated 6 times to maximize the amount of xylan extracted from the starting biomass, and after each cycle, the solids were weighed and set aside, and the aqueous filtrate was recycled back into the reactor. After the sixth reaction cycle, the filtrate (approx. 250 mL) was collected and a sufficient amount of a fresh, aqueous 1% $H_2SO_4$ solution was added to the collected filtrate to bring the total weight of the filtrate to 300 g; a sample was taken for analysis and the rest used in an acid dehydration reaction.

Acid Dehydration: To the filtrate of the $6^{th}$ digestion cycle from above in a batch reactor 300 g of toluene was added (water:solvent weight ratio of 1:1) as an immiscible extracting organic solvent, the reactor was heated to 170° C., and maintained at that temperature for 1 hour. The contents of the reactor were filtered to separate any insoluble solids that had formed in the mixture from the liquid product stream containing an aqueous phase and an organic phase. The liquid fraction was separated into an aqueous product and an organic product, and small fractions (2-5 ml) were taken for analysis. Aqueous phase was analyzed using HPLC and the organic phase using GC. The organic phase was set aside, and the aqueous phase (which was acidic in pH due to the $H_2SO_4$) was recycled back to the Zipperclave batch reactor for the digestion of 30 g of fresh bagasse as described above. A 1% aqueous $H_2SO_4$ solution was added (as appropriate) to the recycled aqueous phase to a weight of 300 g.

Overall, the digestion and acid dehydration steps were repeated with the recycled aqueous phase from dehydration three times (which includes the internal six recycle loops during the digestion), with the organic phase (toluene) being recycled to build furfural concentration.

Figure 5:
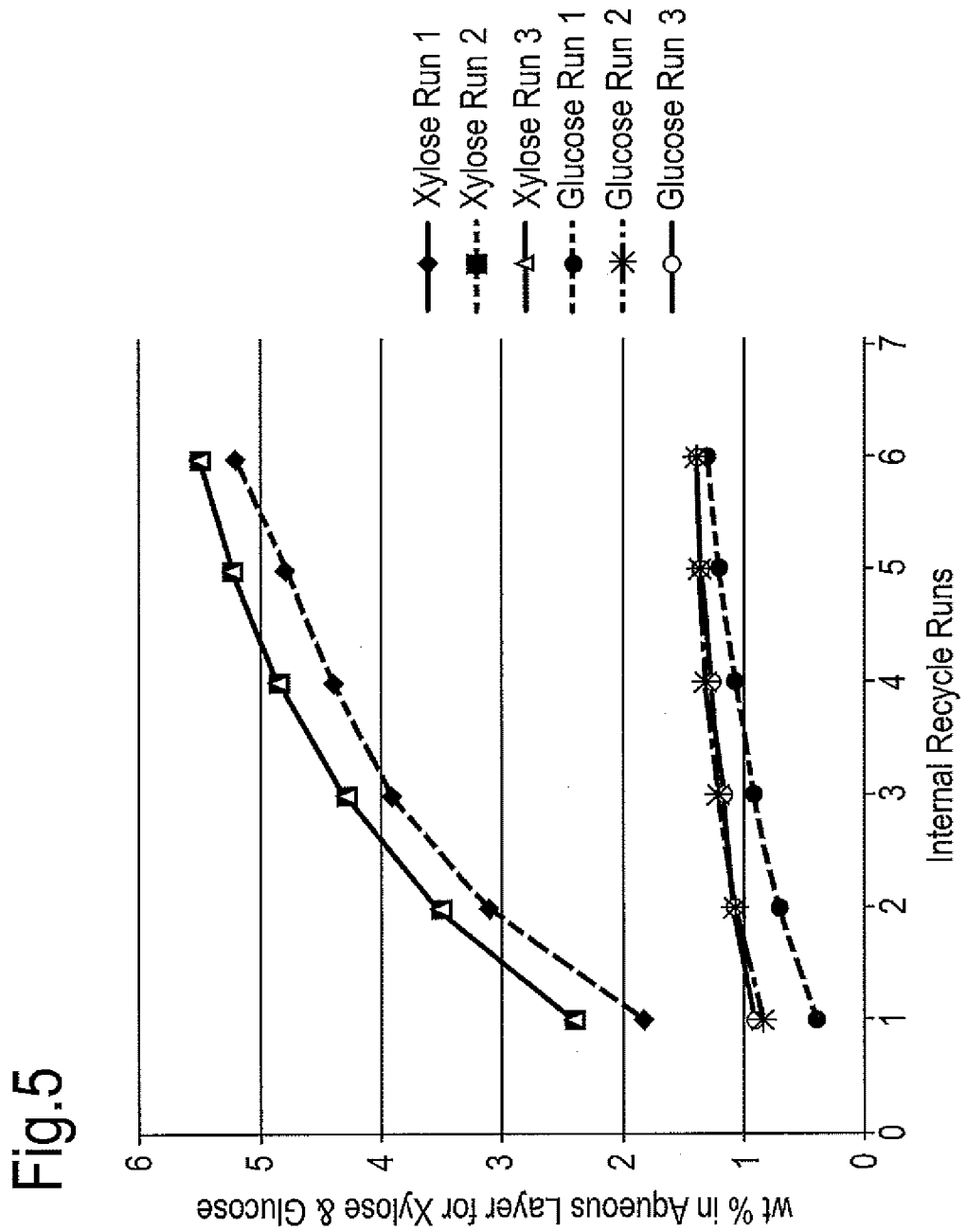
FIG. 5 illustrates the xylose and glucose concentrations for three aqueous acid stream recycle runs.

FIG. 5 shows the xylose and glucose concentrations for three aqueous acid stream recycle runs. FIG. 5 shows that xylose concentration builds up to about 5-5.5 wt % via six internal recycle loop of aqueous stream along with glucose buildup of about 1 wt % coming from cellulose portion of the bagasse. Overall the aqueous phase from biphasic dehydration is recycled to the digestion step to allow for fresh build a steady state xylose concentration each time to about 5 wt % levels.

Figure 6:
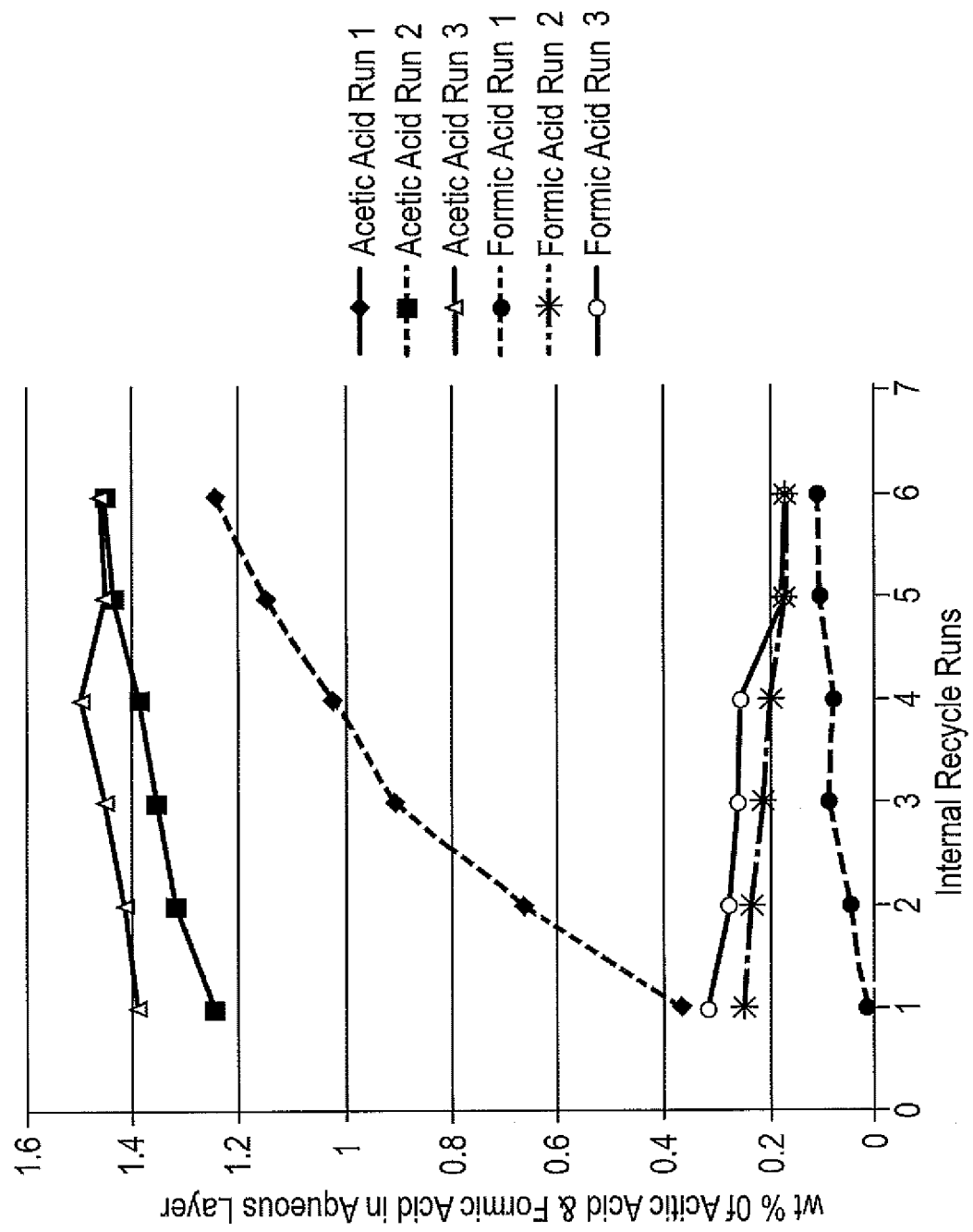
FIG. 6 illustrates the buildup of acetic and formic acid levels through internal and external aqueous stream recycle.

Similarly, FIG. 6 shows the buildup of acetic and formic acid levels through internal and external aqueous stream recycle. The constant level of acetic acid levels (1.2-1.5 wt %) indicates the steady levels of acid build up and minimal takeover of acid in the organic solvent as desired.

Figure 7:
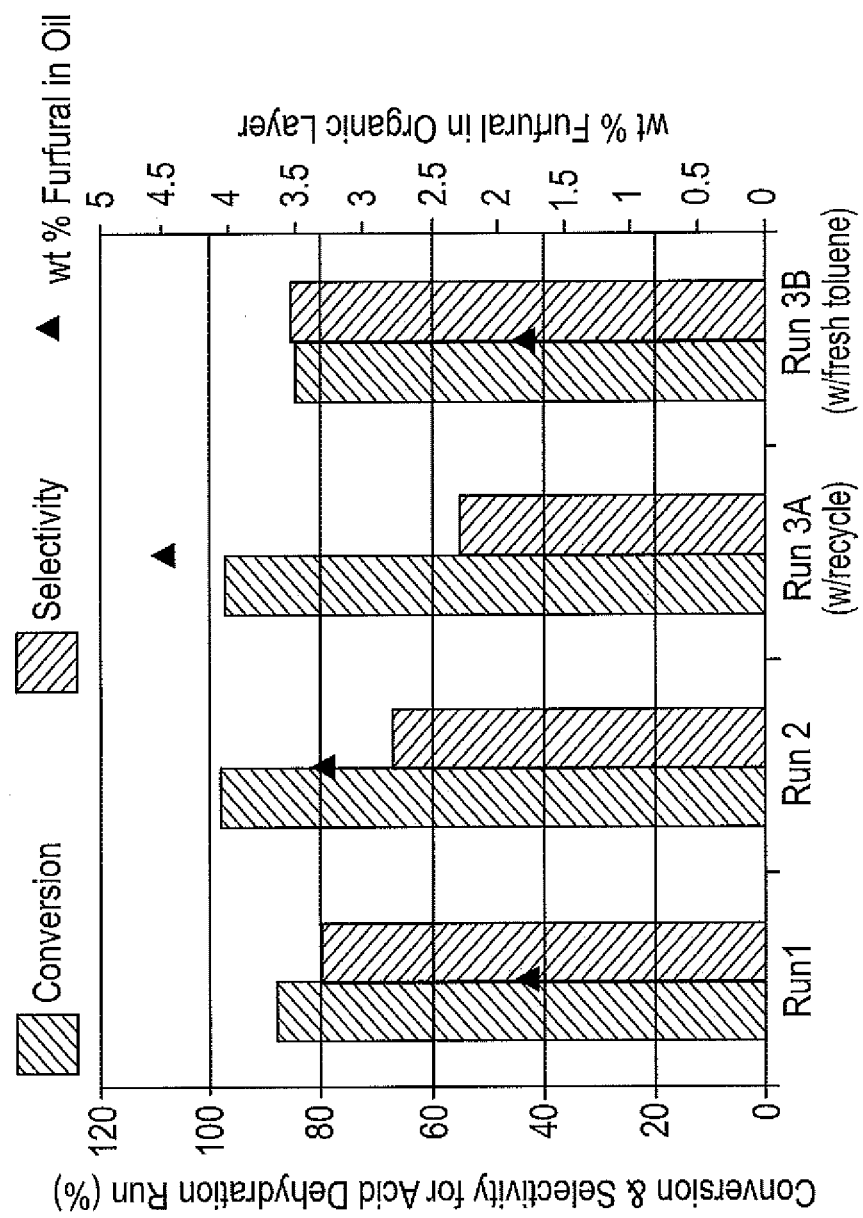
FIG. 7 illustrates the conversion and selectivity towards furfural (left axis) and furfural concentration in organic solvent (right axis) for three aqueous acid stream recycle runs.

FIG. 7 shows the conversion and selectivity towards furfural (left axis) and furfural concentration in organic solvent (right axis) for three aqueous acid stream recycle runs. FIG. 7 shows the conversion of xylose and selectivity towards furfural along with buildup of furfural in the organic solvent due to solvent recycle. It can be seen that furfural selectivity drops with recycle of solvent due to degradation of furfural from the retained furfural in the organic phase. However, by returning the fresh toluene for the last run it shows similar levels of selectivity as the first run with fresh solvent indicating the drop in selectivity by solvent recycle is due to furfural degradation reaction at the biphasic reactor conditions. Indeed, this example demonstrates the recycle of acidified aqueous phase for doing the digestion and dehydration reaction thereby minimizing the overall water usage of the process making it more efficient.

Example 5

Furfural Yield Time Profile with and without an Extracting Solvent

Various runs were conducted to understand the impact of extracting solvent on furfural yield. In a typical run, 100 g of 5 wt % xylose solution (which can be assumed to be produced via digestion runs) was prepared along with 1 wt % $H_2SO_4$ acid concentration. One run was conducted without adding any extracting solvent. For rest of the runs, equal amount (100 g) of extracting organic solvent such as Sec butylphenol (SBP), Toluene or Eugenol is added to the reactor to create a biphasic reaction medium. The reactor was then heated to 170° C. and samples were taken at various times to measure furfural yield. After the reaction is complete the reactor is cooled to room temperature and the two liquid phases are separated. The aqueous phase was analyzed using HPLC and organic phase using GC for its content. The furfural yield from various runs is indicated in FIG. 8.

Figure 8:
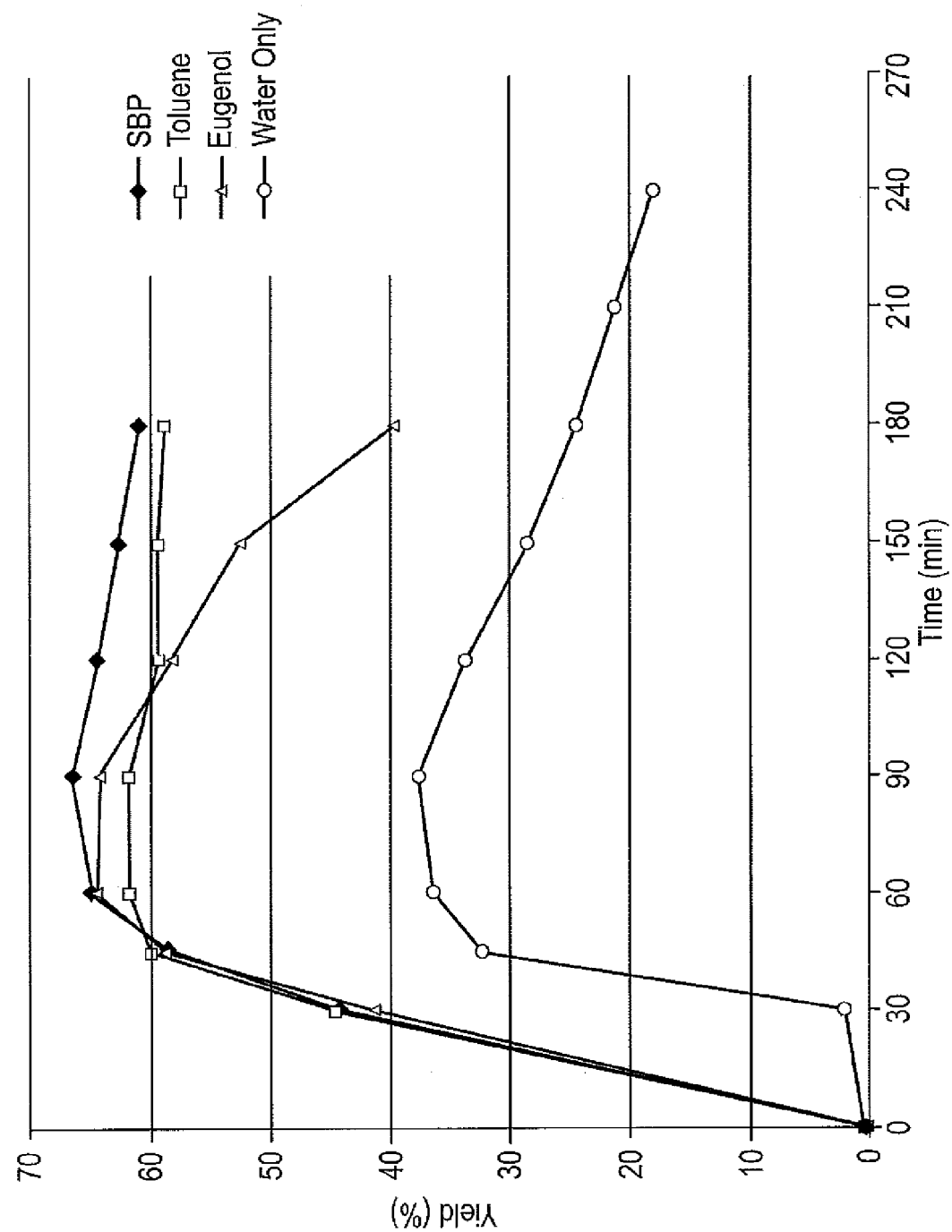
FIG. 8 illustrates furfural yield from various runs.

As seen in FIG. 8, the maximum yield in the presence of water without extracting solvent is about 35%. Whereas, the yield is almost doubled by use of any extracting solvent which prevents furfural degradation loss.

That which is claimed is:

1. A closed-loop process for converting biomass into furfural, the process comprising the steps of:
    (a) providing a pentosan-containing biomass material;
    (b) subjecting the pentosan-containing biomass material to an acid catalyzed digestion process in a digestion vessel at a temperature greater than about 100 ° C. for a period of time sufficient to produce a digested product stream comprising $C_5$-carbohydrates and solids comprising cellulose;
    (c) separating the digested product stream into a liquid product stream and a solid product stream, the liquid product stream comprising carbohydrate compounds, of which carbohydrate compounds at least 50 wt % are $C_5$- carbohydrate compounds, based on the weight of carbohydrate compounds in the liquid product stream, and the solid product stream comprising solids comprising cellulose;
    (d) subjecting the $C_5$-carbohydrate in the liquid product stream to a dehydration reaction in a reaction vessel at a temperature in the range of from about 100 ° C. to about 250 ° C. in the presence of an acid catalyst and a biphasic mixture comprising an aqueous phase and a water-immiscible organic phase, which comprises an organic solvent, for a period of time sufficient to produce furfural or a furan derivative comprising tetrahydrofuran (THF), furan, and 2-methyl THF;
    (e) retrieving from the reaction vessel a dehydration product stream comprising water, organic solvent and comprising furfural and separating the dehydration product stream into an aqueous recycle stream and an organic product stream comprising furfural;
    (f) recycling the aqueous recycle stream back into the digestion vessel in step (b); and
    (g) extracting the furfural from the organic product stream by at least one separation process.

2. The process of claim 1, wherein the aqueous recycle stream comprises the acid catalyst.

3. The process of 1, wherein the mixture comprising pentosan containing biomass material and water has a solid-to-liquid weight ratio ranging from about 1:3 to about 1:30.

4. The process of claim 3, wherein the mixture comprising pentosan containing biomass material and water has a solid-to-liquid ratio ranging from about 1:6 to about 1:10.

5. The process of claim 1, wherein the acid catalyst in the digestion process, the dehydration process, or both is selected from the group consisting of inorganic acids and organic acids.

6. The process of claim 1, wherein the acid catalyst in the digestion process, the dehydration process, or both, is a mineral acid selected from the group consisting of HCl, $HNO_3$, $H_2SO_4$, $H_3PO_4$, and $H_3BO_3$.

7. The process of claim 1, wherein the liquid product stream separated from the solid product stream following digestion comprises $C_5$ carbohydrates in a concentration ranging from about 0.1 wt % to about 15 wt %.

8. The process of claim 7, wherein the liquid product stream comprises $C_5$ carbohydrates in a concentration ranging from about 0.2 wt % to about 10 wt %.

9. The process of claim 1, wherein the aqueous recycle stream in step (f) comprises salts and the aqueous recycle stream is treated to remove at least part of the salts.

10. The process of claim 1, wherein the solid product stream comprises $C_5$-carbohydrate and at least part of the aqueous recycle stream from step (f) is contacted with the solid product stream to extract at least part of the $C_5$-carbohydrate.

11. The process of claim 1, wherein part of the liquid product stream from step (f) is directly recycled to the digestion vessel in step (b).

12. The process of claim 1, wherein part of the organic product stream comprising furfural or the furan derivative from step (e) is directly recycled to the dehydration reaction of step (d).

13. The process of claim 1, wherein solids in the solid product stream are converted into alcohol by hydrolysis and fermentation, glycol by hydrolysis or catalytic conversion, acid by fermentation or chemical conversion, power or energy by burning or otherwise treating the solids in a power plant or similar power production facility, or a fuel gas by gasification methods.

* * * * *